United States Patent
Lebre et al.

(10) Patent No.: US 8,563,015 B2
(45) Date of Patent: Oct. 22, 2013

(54) COSMETIC COMPOSITION COMBINING AN ETHYLENIC ESTER OF TRANS CONFIGURATION AND A HYDROCARBON WAX

(75) Inventors: Caroline Lebre, Thiais (FR); Vanina Filippi, Paris (FR)

(73) Assignee: L'Oreal, Paris (FR)

( * ) Notice: Subject to any disclaimer, the term of this patent is extended or adjusted under 35 U.S.C. 154(b) by 1137 days.

(21) Appl. No.: 11/028,562

(22) Filed: Jan. 5, 2005

(65) Prior Publication Data

US 2005/0226833 A1 Oct. 13, 2005

Related U.S. Application Data

(60) Provisional application No. 60/537,000, filed on Jan. 20, 2004.

(30) Foreign Application Priority Data

Jan. 5, 2004 (FR) ..................................... 04 50003

(51) Int. Cl.
*A61K 8/02* (2006.01)

(52) U.S. Cl.
USPC .............................. 424/401; 424/64; 514/844

(58) Field of Classification Search
None
See application file for complete search history.

(56) References Cited

U.S. PATENT DOCUMENTS

| | | | |
|---|---|---|---|
| 3,957,495 A * | 5/1976 | Teranishi et al. | 106/31.16 |
| 4,360,387 A | 11/1982 | Brown et al. | |
| 4,393,043 A | 7/1983 | Koulbanis et al. | |
| 4,591,602 A * | 5/1986 | De Villez | 514/463 |
| 5,968,530 A | 10/1999 | Arquette | |
| 6,375,938 B1 * | 4/2002 | Clothier et al. | 424/65 |
| 6,585,985 B2 * | 7/2003 | Sakuta | 424/401 |
| 7,129,276 B2 * | 10/2006 | Ferrari | 514/772.3 |
| 2003/0049219 A1 * | 3/2003 | Lemoine et al. | 424/66 |
| 2003/0124153 A1 * | 7/2003 | Opel et al. | 424/401 |

FOREIGN PATENT DOCUMENTS

| | | |
|---|---|---|
| EP | 0 542 669 A1 | 5/1993 |
| EP | 0 787 730 A1 | 8/1997 |
| EP | 0 787 731 A2 | 8/1997 |
| EP | 1 410 784 A1 | 4/2004 |
| EP | 1 410 787 A1 | 4/2004 |
| FR | 2844190 A1 | 3/2004 |
| WO | WO 96/08537 A1 | 3/1996 |
| WO | WO 03/000223 A1 * | 1/2003 |

OTHER PUBLICATIONS

Ozokerite [online], [retrieved Jul. 16, 2008], Retrieved from Encyclopedia Britannica using Internet <URL: http://www.britannica.com/EBchecked/topic/437187/ozokerite>, 2008.*
Gondoic acid, Substance summary [online], [retrieved Jul. 16, 2008], Retrieved from PubChem using internet <URL: http://pubchem.ncbi.nlm.nih.gov/summary/summary.cgi?sid=8147780>, 2008.*
Erucyl alcohol, Substance summary [online], [retrieved Jul. 16, 2008], Retrieved from PubChem using internet <URL: http://pubchem.ncbi.nlm.nih.gov/summary/summary.cgi?cid=5354168>, 2008.*
White Ozokerite Wax (White Ozokerite Wax, [online], Retrieved [Nov. 4, 2009], Retrieved from URL:<http://www.spwax.com/spceresi.htm>.*
SOFTISAN 100, Product Information, [online Sep. 13, 2010], Retrieved from URL:<http://www.warnergraham.com/images/Softisan100ProdInfo.pdf>.*
The Chemistry and Manufacture of Cosmetics, vol. II, Ed. 3, pp. 629-657, Allured Pub. 2000.
The Chemistry and Manufacture of Cosmetics, vol. III, Book II, Ed. 3, pp. 1104-1107, Allured Pub. 2002.

* cited by examiner

*Primary Examiner* — Lezah Roberts
*Assistant Examiner* — Nannette Holloman
(74) *Attorney, Agent, or Firm* — Oliff & Berridge plc

(57) ABSTRACT

A cosmetic composition for caring for and/or making up the skin, lips and/or keratinous substances combines at least one ester of a $C_{16}$ to $C_{24}$ ethylenic acid and of a $C_{16}$ to $C_{24}$ ethylenic alcohol, said acid and/or said alcohol being of trans configuration, with at least one hydrocarbon wax with a melting point of greater than 70° C.

26 Claims, No Drawings

COSMETIC COMPOSITION COMBINING AN ETHYLENIC ESTER OF TRANS CONFIGURATION AND A HYDROCARBON WAX

This nonprovisional application claims the benefit of U.S. Provisional Application No. 60/537,000, filed Jan. 20, 2004.

BACKGROUND

Cosmetic compositions that possess improved properties in terms of application, of comfort, of mechanical strength and of stability are provided.

More particularly, the cosmetic compositions of embodiments relate to the making up and/or caring for the skin and superficial body growths. Generally, cosmetic compositions have to give satisfaction in terms of comfort. More particularly, cosmetic compositions have to be sufficiently unctuous to provide, on application, a melting, soft and slip effect while being sufficiently structured to be taken up with the finger or to be packaged, for example in a pot, as a pen or as a stick.

The compositions of the prior art that are easy to apply and creamy on application often lack stability over time; whether because the oils they comprise migrate to the surface of the composition, which becomes shiny (phenomenon of exudation or of phase separation), or because the waxes which they comprise undergo a phenomenon of recrystallization, with the result that the composition becomes matte.

In addition, in the case of solid compositions, when seeking to increase the amount of the composition coating on keratinous substances in a single operation or when desiring to render the coating more flexible on application, the mechanical strength of the composition generally becomes inadequate, with the result that the composition breaks down or becomes flattened when the user applies it and with the result that the composition can no longer be used.

Thus, it is very difficult to obtain a cosmetic composition exhibiting both good application properties, such as softness, unctuousness, creaminess, and an acceptable structure, that is to say one which can withstand temperatures of the order of 38° C., and retaining a smooth and unblemished surface appearance over time, without exudation or crystallization.

U.S. Pat. No. 4,360,387 discloses cosmetic compositions comprising a mixture of hydrogenated jojoba oil and of jojoba butter. However, these compositions exhibit the disadvantage of exuding over time or of not being sufficiently creamy on application.

SUMMARY

The inventors have found that it is possible to obtain a composition possessing both a satisfactory mechanical strength and an improved application qualities. This composition comprises, in embodiments, at least one hydrocarbon wax having a relatively high melting point and at least one unsaturated ester having a relatively low melting point.

Specifically, the inventors have found that, by combining, with an unsaturated ester, such as jojoba butter, a hydrocarbon wax with a sufficiently high melting point, it is possible to obtain a cosmetic composition that, in embodiments overcomes the abovementioned disadvantages.

More specifically, embodiments of the present invention relate to a cosmetic composition, in particular for caring for and/or making up the skin, lips and/or keratinous substances, which combines, with at least one ester of a $C_{16}$ to $C_{24}$ ethylenic acid and of a $C_{16}$ to $C_{24}$ ethylenic alcohol, with said acid and/or alcohol being of trans configuration, at least one hydrocarbon wax with a melting point of greater than 70° C.

Surprisingly, the combination of a hydrocarbon wax with a high melting point with this type of ester makes it possible to confer, on the cosmetic compositions of embodiments, the desired mechanical properties without prejudicing their properties in terms of comfort. Thus, the cosmetic compositions according to embodiments of the invention prove to have good application properties reflected in particular by a feeling of melting, of slip, of unctuousness and of softness.

The compositions of embodiments of the invention also exhibit a satisfactory mechanical and thermal stability over time that is all the more surprising as the compositions of the prior art, exhibiting slip on application, generally exhibit insufficient stability.

Compositions according to embodiments of the invention are not subject to the phenomena of recrystallization over time, which phenomena are, of course, harmful in terms of attractiveness, since recrystallization gives the surface of the composition a matte appearance. The compositions of embodiments may also exhibit the advantage of not exuding over time.

In addition, embodiments of the invention use the combination of at least one ester of a $C_{16}$ to $C_{24}$ ethylenic acid and of a $C_{16}$ to $C_{24}$ ethylenic alcohol, said acid and/or said alcohol being of trans configuration, and of at least one hydrocarbon wax with a melting point of greater than 70° C. in a cosmetic composition for improving its comfort, its slip on application and its unctuousness while retaining its mechanical properties.

DETAILED DESCRIPTION OF EMBODIMENTS

The composition according to embodiments comprises at least one ester of a $C_{16}$ to $C_{24}$ ethylenic acid and of a $C_{16}$ to $C_{24}$ ethylenic alcohol with said acid and/or said alcohol being of trans configuration.

According to embodiments, the cosmetic composition is solid in the sense that it exhibits a specific hardness. The hardness of the cosmetic composition can be measured by the "cheese wire" method, which consists in cutting a stick of the test composition with a diameter of between 8 and 12.7 mm and in measuring the hardness at 20° C. using a DFGHS 2 dynamometer from Indelco-Chatillon moving at a rate of 100 mm/minute. Hardness is expressed as the shear force (expressed in grams) necessary to cut a stick under these conditions. According to this method, the hardness of the composition according to embodiments of the invention varies from 40 to 250 g, in particular from 60 to 190 g and more particularly from 80 to 170 g.

Herein, the term "a $C_{16}$ to $C_{24}$ ethylenic acid" denotes a $C_{16}$ to $C_{24}$ hydrocarbon compound comprising at least one ethylenic unsaturation and at least one carboxyl functional group.

The term "hydrocarbon compound" is understood to mean a compound composed essentially of carbon and of hydrogen and optionally functionalized by a group comprising a heteroatom, such as oxygen, nitrogen or halogen.

According to specific embodiments, the ethylenic acid is devoid of any functionalized group other than the carboxyl functional group. In particular, it is devoid of a hydroxyl group.

The ethylenic acid can exhibit a single carboxyl functional group or several carboxyl functional groups. Advantageously, it carries a single carboxyl functional group. The ethylenic acid in accordance with embodiments can be linear or branched. In particular embodiments, it is linear. The ethylenic acid comprises at least one ethylenic unsaturation, and, in particular embodiments, it comprises a single ethylenic unsaturation. The ethylenic acid of embodiments may comprise from 16 to 24 carbon atoms, in particular from 20 to 22 carbon atoms.

By way of representation of the type of acids suitable for use in embodiments of the invention, mention may be made of compounds with the following formula:

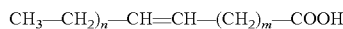

$$CH_3—(CH_2)_n—CH=CH—(CH_2)_m—COOH$$

in which the sum of n and m varies from 14 to 20, n and m denoting natural integers. In particular, m varies from 8 to 12.

For example, the ethylenic acid is chosen from the group consisting of octadec-9-enoic acid or oleic acid ($C_{18}$), eicos-11-enoic acid ($C_{20}$), docos-13-enoic acid or erucic acid ($C_{22}$), such as n=7 and m=11, tetracos-15-enoic acid ($C_{24}$) and their mixtures.

Herein, the term "a $C_{16}$ to $C_{24}$ ethylenic alcohol" denotes a $C_{16}$ to $C_{24}$ hydrocarbon compound comprising at least one ethylenic unsaturation and at least one hydroxyl functional group.

This alcohol can exhibit a single hydroxyl functional group or several hydroxyl functional groups. Advantageously, it carries a single hydroxyl functional group. According to specific embodiments, the ethylenic alcohol is devoid of any functionalized group other than the hydroxyl functional group.

The alcohol in accordance with embodiments can be branched or linear. In particular embodiments, the alcohol is linear. The alcohol of embodiments comprises at least one ethylenic unsaturation. In particular, it comprises a single ethylenic unsaturation. The ethylenic alcohol in accordance with embodiments can be chosen from $C_{20}$ and $C_{22}$ alcohols.

According to specific embodiments, the ethylenic alcohol corresponds to the following general formula:

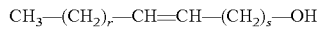

$$CH_3—(CH_2)_r—CH=CH—(CH_2)_s—OH$$

in which the sum of r and s varies from 15 to 21, r and s denoting natural integers. In particular, s varies from 10 to 14.

Mention may in particular be made, by way of illustration of the alcohols suitable for embodiments, of octadec-9-enol ($C_{18}$), eicos-11-enol ($C_{20}$), docos-13-enol ($C_{22}$), tetracos-15-enol ($C_{24}$) or one of their mixtures.

As specified above, the ester according to embodiments of the invention has at least one ethylenic unsaturation or ethylenic bond of trans configuration, either on the alkyl radical or on the alkanoyl radical of the molecule. According to specific embodiments, the ester has two ethylenic bonds of trans configuration, one situated on the alkyl radical and the other situated on the alkanoyl radical of the molecule.

According to specific embodiments, the ester comprises from 38 to 44 carbon atoms. It can be chosen in particular from the group consisting of eicos-11-enyl oleate, eicos-11-enyl eicos-11-enoate, docos-13-enyl eicos-11-enoate, tetracos-15-enyl eicos-11-enoate, eicos-11-enyl docos-13-enoate and their mixtures.

More particularly, the composition of embodiments comprises the ester as defined above in the form of a mixture.

According to specific embodiments, said ester is introduced into the composition in the form of jojoba butter.

Jojoba butter can be obtained from jojoba oil, extracted from the seed of the species *Simmondsia chinensis*, for example according to the process disclosed in U.S. Pat. No. 4,329,298. The jojoba butters sold under the names "ISO-JOJOBA 35%" and "ISO-JOJOBA 50®" by Desert Whale Jojoba Company, in particular, are thus suitable for use in embodiments of the invention.

In particular embodiments, a jojoba butter is chosen from those having a melting point of less than 60° C., in particular ranging from 35 to 50° C. The melting point is measured at the tip of the most endothermic peak of the thermogram plotted using a differential scanning calorimeter (DSC), such as the calorimeter sold under the name "MDSC 2920®" by TA Instrument, with a temperature rise of 5 or 10° C. per minute, according to standard ISO 11357-3:1999.

Jojoba butter may be advantageously present in the composition according to embodiments in an amount in a range of from 0.1 to 40%, for example from 0.5 to 15%, in particular from 1 to 12% and more particularly from 1.5 to 8%, by weight. For obvious reasons, this proportion is, of course, capable of significantly varying according to the nature of the cosmetic composition under consideration.

In addition, the composition according to embodiments comprises at least one hydrocarbon wax having a melting point of greater than 70° C.

The term "wax" herein is understood to mean a lipophilic fatty compound, which is solid at ambient temperature (25° C.), which exhibits a reversible solid/liquid change of state, which has a melting point of greater than or equal to 30° C. which can range up to 200° C., which has a hardness of greater than 0.5 MPa and which exhibits, in the solid state, an anisotropic crystalline arrangement.

The term "hydrocarbon wax" is understood to mean a wax composed solely of carbon and of hydrogen.

The hydrocarbon wax in accordance with embodiments of the invention can be chosen in particular from microcrystalline waxes, polyethylene waxes, Fischer-Tropsch waxes, paraffin waxes, and their mixtures, with the proviso that said wax exhibits a melting point, measured according to the method described above, of greater than 70° C.

The wax having a melting point of greater than 70° C. can be present in the compositions according to embodiments in a proportion of 0.1 to 25% by weight, in particular of 2 to 20% by weight, especially of 3 to 15% by weight and more particularly of 5 to 12% by weight, with respect to the total weight of the composition.

The hydrocarbon wax in accordance with embodiments has in particular a melting point of less than or equal to 105° C., in particular ranging from 75° C. to 100° C. and more particularly from 80 to 95° C.

According to specific embodiments, the composition comprises at least two different hydrocarbon waxes.

In embodiments, these waxes are distinguished by their structures, some of them being linear and the others being branched. Thus, the composition of embodiments of the invention advantageously comprises the mixture of at least one linear hydrocarbon wax and of at least one branched hydrocarbon wax. It can, in particular embodiments, be a mixture of at least one polyethylene wax and of at least one microcrystalline wax, or a mixture of at least one paraffin wax and of at least one microcrystalline wax.

In embodiments, the composition comprises a mixture of at least two hydrocarbon waxes having different melting points. The compositions according to embodiments can in particular comprise a mixture of at least one wax having a melting point of greater than 70° C. and which can range up to 80° C. inclusive and of at least one wax having a melting point of greater than 80° C. and in particular of less than or equal to 105° C.

Advantageously, in embodiments, the ratio by weight of wax having a melting point of greater than 70° C. and of less than or equal to 80° C. to wax having a melting point of greater than 80° C. is from 1/1 to 3/1, and in particular approximately 2/1.

These waxes, which are distinguished by their melting points, can also be distinguished by their structures, it being possible for one to be of linear type and for the other to be of branched type. Furthermore, the composition according to embodiments can comprise a mixture of waxes with different melting points as is defined above with, for a given melting point range or for a given melting point, a mixture of waxes that exhibit different structures of linear and branched type. The hydrocarbon wax in accordance with embodiments is advantageously a polyethylene wax. Herein, the expression "polyethylene wax" is understood to mean a polymer chosen from ethylene homopolymers and copolymers of ethylene and of a monomer corresponding to the formula:

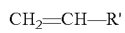

in which:

R' represents an alkyl radical having from 1 to 30 carbon atoms or an aryl or aralkyl radical.

The term "polymer" is understood to mean a compound comprising at least 2 repeat units, in particular at least 3 repeat units and more particularly at least 10 repeat units.

Mention may be made, among alkyl radicals having from 1 to 30 carbon atoms that may be used in accordance with embodiments of the invention, of the methyl, ethyl, propyl, isopropyl, decyl, dodecyl and octadecyl radicals. The aryl radical may, in particular embodiments, be a phenyl or tolyl radical. The aralkyl radical may, in particular embodiments, be a benzyl or phenethyl radical. As these waxes are synthetic products, they do not exhibit the problems of variability observed with natural compounds.

According to specific embodiments of the compositions, the wax used as defined above is chosen from ethylene homopolymers, ethylene/propylene copolymers and ethylene/hexene copolymers, and advantageously from ethylene homopolymers.

Advantageously, the polyethylene wax used in the compositions of embodiments exhibits a melting point, measured according to the calorimetry method described above, of greater than 70° C. and of less than or equal to 105° C., in particular ranging from 80 to 95° C. According to specific embodiments of the compositions, the polyethylene waxes are chosen from polymers, and in particular homopolymers, having a molecular weight ranging from 300 to 700, in particular from 350 to 650. Mention may in particular be made, as ethylene homopolymers that can be used in the compositions according to embodiments, of the waxes sold under the names of "PERFORMALEN 500®" and "PERFORMALEN 400®" by Newphase Technologies, having molecular weights of 500 and 400 respectively. Mention may in particular be made, among the ethylene copolymers that can be used according to embodiments, of the ethylene/propylene copolymers sold under the name of "PERFORMALEN EP 700®" by Newphase Technologies.

According to embodiments, use may be made of a mixture of polyethylene waxes exhibiting different melting points. In particular embodiments, use may be made of a mixture of at least one polyethylene wax having a melting point of greater than 70° C. and of less than or equal to 80° C. and of at least one polyethylene wax having a melting point of greater than 80° C. and of less than or equal to 105° C. Advantageously, the composition according to embodiments comprises a mixture of at least one polyethylene wax having a melting point of less than or equal to 75° C. and of at least one polyethylene wax having a melting point of greater than 80° C. and of less than or equal to 90° C.; such a mixture may be present in a ratio by weight in the range of from 1/1 to 3/1 and especially in a ratio by weight of approximately 2/1.

Advantageously, the ester and the wax required in the context of embodiments are combined in the cosmetic composition in an ester/wax ratio by weight generally of less than 1 and that can in particular range from 0.15 to 0.75.

According to particular embodiments, the composition comprises from 0.1 to 40% of jojoba butter and from 0.1 to 25% of hydrocarbon wax, in particular from 0.5 to 15% of jojoba butter and from 2 to 20% of wax and more particularly from 1% to 12% of jojoba butter and from 3 to 15% of wax, said percentages being expressed by weight with respect to the total weight of the composition.

Of course, other cosmetic additives can be combined with the wax and the ester according to embodiments so as to confer on the cosmetic composition under consideration the desired properties, in particular in terms of melting point, fluidity and mechanical strength.

Thus, the cosmetic compositions according to embodiments of the invention, in particular when the cosmetic compositions are intended to be applied to the lips, skin and eyelashes, can comprise an additional fatty substance other than the ester and the wax that are described above, in particular at least one fatty substance that is liquid at ambient temperature (25° C.) and at atmospheric pressure.

The composition of embodiments can have, for example, a continuous fatty phase that can comprise less than 5% of water, in particular less than 1% of water, with respect to its total weight and can in particular be in the anhydrous form. The fatty phase can comprise, in particular embodiments, as liquid fatty substance, at least one volatile or nonvolatile oil or one of their mixtures.

Herein, the term "volatile oil" is understood to mean any oil capable of evaporating on contact with the skin in less than one hour at ambient temperature and atmospheric pressure. The volatile oils of embodiments are volatile cosmetic oils that are liquid at ambient temperature and that have a nonzero vapor pressure, at ambient temperature and atmospheric pressure, ranging in particular from 0.01 to 300 mm of Hg (1.33 Pa to 40 000 Pa) and more particularly of greater than 0.3 mm of Hg (30 Pa).

The term "nonvolatile oil" is understood to mean an oil having in particular a vapor pressure of less than 0.01 mm of Hg (1.33 Pa).

These volatile or nonvolatile oils can be hydrocarbon oils, in particular embodiments, hydrocarbon oils of vegetable origin; silicone oils, or their mixtures. The term "hydrocarbon oil" is understood to mean an oil comprising mainly hydrogen and carbon atoms and optionally oxygen, nitrogen, sulfur and/or phosphor atoms.

Volatile hydrocarbon oils of embodiments of the invention can be chosen from hydrocarbon oils having from 8 to 16 carbon atoms and in particular branched $C_8$-$C_{16}$ alkanes, such as $C_8$-$C_{16}$ isoalkanes of petroleum origin (also known as isoparaffins), such as isododecane (also known as 2,2,4,4,6-pentamethylheptane), isodecane, isohexadecane and, for example, those sold under the ISOPAR® or PERMETYL® trade names, $C_8$-$C_{16}$ branched esters, such as isohexyl neopentanoate, and their mixtures. Other volatile hydrocarbon oils, such as petroleum distillates, in particular those sold under the name Shell SOLT® by Shell, can also be used. In embodiments, use may also be made, as volatile oils, of volatile silicones, such as, for example, volatile linear or cyclic silicone oils, in particular those having a viscosity ≤8 centistokes ($8 \times 10^{-6}$ m$^2$/s), and having in particular from 2 to 7 silicon atoms, these silicones optionally comprising alkyl or alkoxy groups having from 1 to 10 carbon atoms. Mention may in particular be made, as volatile silicone oil that can be used in embodiments, of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane, dodecamethylpentasiloxane and their mixtures.

The volatile oil can be present in the composition according to embodiments in amounts in a range of from 0.01 to 50% by weight, in particular from 0.1 to 40% by weight and especially from 1 to 30% by weight, with respect to the total weight of the composition.

Nonvolatile oils in particular embodiments can be chosen from nonvolatile hydrocarbon oils, if appropriate fluorinated, and/or nonvolatile silicone oils. Mention may in particular be made, as nonvolatile hydrocarbon oil, of:

hydrocarbon oils of animal origin;

hydrocarbon oils of vegetable origin, such as triglycerides composed of esters of fatty acids and of glycerol, the fatty acids of which can have various chain lengths from $C_4$ to $C_{24}$, it being possible for these chains to be linear or branched and saturated or unsaturated; these oils are, in particular, wheat germ, sunflower, grape seed, sesame, corn, apricot, castor, karite, avocado, olive, soybean, sweet almond, palm, cottonseed, hazelnut, macadamia, alfalfa, poppy, pumpkinseed, sesame, cucumber, rapeseed, blackcurrant seed, evening primrose, millet, barley, quinoa, rye, safflower, candlenut, passionflower or musk rose oil; karite butter; or triglycerides of caprylic/capric acids, such as those sold by Stéarineries Dubois or those sold under the names MIGLYOL 810®, 812® and 818® by Dynamit Nobel;

synthetic ethers having from 10 to 40 carbon atoms;

linear or branched hydrocarbons of mineral or synthetic origin, such as liquid petrolatum, polydecenes, hydrogenated polyisobutene, such as PARLEAM®, squalane, and their mixtures;

synthetic esters, such as oils of formula $R^1COOR^2$ in which $R^1$ represents the residue of a linear or branched fatty acid comprising from 1 to 40 carbon atoms and $R^2$ represents a hydrocarbon chain, in particular a branched hydrocarbon chain, comprising from 1 to 40 carbon atoms, provided that $R^1+R^2$ is ≥10, such as, for example, PURCELLIN oil (cetearyl octanoate), isopropyl myristate, isopropyl palmitate, $C_{12}$ to $C_{15}$ alkyl benzoates, hexyl laurate, diisopropyl adipate, isononyl isononanoate, 2-ethylhexyl palmitate, isostearyl isostearate, or heptaneoates, octanoates, decanoates or ricinoates of alcohols or of polyalcohols, such as propylene glycol dioctanoate; poly(vinyl laurate); hydroxylated esters, such as isostearyl lactate or diisostearyl malate; polyol esters and pentaerythritol esters;

fatty alcohols that are liquid at ambient temperature with a branched and/or unsaturated carbon chain having from 12 to 26 carbon atoms, such as octyldodecanol, isostearyl alcohol, oleyl alcohol, 2-hexyldecanol, 2-butyloctanol and 2-undecylpentadecanol;

higher fatty acids, such as oleic acid, linoleic acid or linolenic acid, and their mixtures.

The nonvolatile silicone oils that can be used in the composition according to embodiments of the invention can be nonvolatile polydimethylsiloxanes (PDMSs), polydimethylsiloxanes comprising pendant alkyl or alkoxy groups and/or alkyl or alkoxy groups at the end of the silicone chain, which groups each have from 2 to 24 carbon atoms, or phenylated silicones, such as phenyl trimethicones, phenyl dimethicones, phenyl(trimethylsiloxy)diphenylsiloxanes, diphenyl dimethicones, diphenyl-(methyldiphenyl)trisiloxanes and (2-phenylethyl) trimethylsiloxysilicates.

The nonvolatile oils can be present in the composition according to embodiments in amounts in a range of from 0.01 to 90% by weight, in particular from 0.1% to 85% by weight and especially from 1% to 70% by weight, with respect to the total weight of the composition.

According to specific embodiments of the invention, the cosmetic composition comprises at least one silicone oil and/or one nonpolar hydrocarbon oil.

The term "nonpolar hydrocarbon oil" is understood to mean an oil composed solely of carbon and of hydrogen. Such a nonpolar hydrocarbon oil is therefore devoid of polar functional groups, such as hydroxyl or carboxyl groups, and of heteroatoms. Such an oil may be chosen, in particular embodiments, from liquid petrolatum, polydecenes, hydrogenated polydecenes, squalane, polybutene, polyisobutene, hydrogenated polyisobutene or one of their mixtures.

The composition of embodiments may comprise at least 20%, and more particularly at least 30%, by weight with respect to the total weight of the composition, of a silicone oil and/or of a nonpolar hydrocarbon oil as described above.

The composition according to embodiments may comprise in particular less than 40%, especially less than 30% and more particularly less than 30%, by weight with respect to the total weight of the composition, of a polar hydrocarbon oil and in particular of a hydrocarbon oil comprising hydroxyl functional groups.

The composition according to embodiments is in particular devoid of castor oil.

More generally, in embodiments, the fatty substance that is liquid at ambient temperature under atmospheric pressure can be present in a proportion of 0.01 to 90% by weight and in particular of 0.1 to 85% by weight, with respect to the weight of the fatty phase.

In embodiments, the additional fatty substance that is solid at ambient temperature under atmospheric pressure other than the ester and the wax having a melting point of greater than 70° C. that are described above can be chosen from waxes having a melting point of less than or equal to 70° C., pasty fatty substances, gums and their mixtures. This solid fatty substance can be present in a proportion of 0.01 to 50%, in particular of 0.1 to 40% and especially of 0.2 to 30% by weight, with respect to the total weight of the fatty phase.

According to embodiments, the composition can comprise, apart from the wax having a melting point of greater than 70° C., an additional wax. It can be of hydrocarbon, fluorinated and/or silicone nature and can be of animal, vegetable, mineral or synthetic origin. It can be chosen, for example, from beeswax, carnauba wax, candelilla wax and their mixtures.

According to embodiments, the composition is devoid of wax having a melting point of less than or equal to 70° C. In particular, the composition is devoid of ozokerite.

According to embodiments, the cosmetic composition can comprise at least one fatty compound that is pasty at ambient temperature.

Herein, the term "pasty compound" is understood to denote a lipophilic fatty compound with a reversible solid/liquid change of state exhibiting, in the solid state, an anisotropic crystalline arrangement and comprising, at a temperature of 23° C., a liquid fraction and a solid fraction. The term "pasty compound" is also understood to mean a compound having a hardness at 20° C. ranging from 0.001 to 0.5 MPa and in particular ranging from 0.002 to 0.4 MPa.

The hardness is measured according to a method of penetration of a probe into a sample of compound and in particular using a texture analyzer (for example, the TA-XT2i from Rheo) equipped with a stainless steel cylinder with a diameter of 2 mm. The hardness measurement is carried out at 20° C. at the center of 5 samples. The cylinder is introduced into each sample at a pre-rate of 1 mm/s and then at a measuring rate of 0.1 mm/s, the depth of penetration being 0.3 mm. The value recorded for the hardness is that of the maximum peak.

In embodiments, this pasty compound is, at a temperature of 23° C., in the form of a liquid fraction and of a solid fraction. In other words, the starting melting point of the pasty compound is, in embodiments of the invention, less than 23° C. The liquid fraction of the pasty compound, measured at 23° C., may represent 9 to 97% by weight of the compound, or, in particular embodiments, from 15 to 85% or from 40 to 85%, by weight.

In embodiments, the liquid fraction by weight of the pasty compound at 23° C. is equal to the ratio of the enthalpy of fusion consumed at 23° C. to the enthalpy of fusion of the pasty compound. The enthalpy of fusion of the pasty compound is the enthalpy consumed by the compound to change from the solid state to the liquid state. The pasty compound is "in the solid state" when the whole of its mass is in the crystalline solid form. The pasty compound is "in the liquid state" when the whole of its mass is in the liquid form. The enthalpy of fusion of the pasty compound is equal to the area under the curve of the thermogram obtained using a differential scanning calorimeter (DSC), such as the calorimeter sold under the name MDSC 2920 by TA Instrument, with a rise in temperature of 5 or 11° C. per minute, according to the standard ISO 11357-3: 1999. The enthalpy of fusion of the pasty compound is the amount of energy necessary to change the compound from the solid state to the liquid state, expressed in J/g. The enthalpy of fusion consumed at 23° C. is the amount of energy absorbed by the sample to change from the solid state to the state that it exhibits at 23° C., composed of a liquid fraction and of a solid fraction.

In embodiments, the liquid fraction of the pasty compound measured at 32° C. represents in particular from 30 to 100% by weight of the compound, more particularly from 80 to 100%, indeed even from 90 to 100%, by weight of the compound. When the liquid fraction of the pasty compound measured at 32° C. is equal to 100%, the temperature of the end of the melting range of the pasty compound is less than or equal to 32° C.

In embodiments, the liquid fraction of the pasty compound measured at 32° C. is equal to the ratio of the enthalpy of fusion consumed at 32° C. to the enthalpy of fusion of the pasty compound. The enthalpy of fusion consumed at 32° C. is calculated in the same way as the enthalpy of fusion consumed at 23° C.

The pasty compound may be chosen, in embodiments, from:
polymeric or nonpolymeric silicone compounds,
polymeric or nonpolymeric fluorinated compounds,
vinyl polymers, in particular:
  homopolymers of olefins,
  copolymers of olefins,
  hydrogenated homopolymers and copolymers of dienes,
  homo- or copolymeric, linear or branched, oligomers of alkyl (meth)acrylates preferably having a $C_8$-$C_{30}$ alkyl group,
  homo- and copolymeric oligomers of vinyl esters having $C_8$-$C_{30}$ alkyl groups,
  homo- and copolymeric oligomers of vinyl ethers having $C_8$-$C_{30}$ alkyl groups,
fat-soluble polyethers resulting from the polyetherification between one or more $C_2$-$C_{100}$, in particular $C_2$-$C_{50}$, diols,
esters,
and their mixtures.

The pasty compound is, in embodiments, of polymer type, in particular of hydrocarbon type.

The cosmetic composition of embodiments can, in addition, comprise a particulate phase that can be present in a proportion of 0.01 to 40% by weight, in particular of 0.01 to 30% by weight and especially of 0.05 to 20% by weight, with respect to the total weight of the composition.

The particulate phase of embodiments can comprise dyes and/or pigments and/or additional fillers used in cosmetic compositions.

The term "pigments" should be understood as meaning white or colored and inorganic or organic particles that are intended to color and/or opacify the composition. The pigments include pearlescent agents, which are iridescent particles produced in particular by certain shellfish in their shells or else synthesized. The term "fillers" should be understood as meaning colorless or white, inorganic or synthetic and lamellar or nonlamellar particles.

The pigments can be present in the composition of embodiments in a proportion of 0.01 to 25% by weight, in particular of 0.01 to 15% by weight.

Mention may be made, as inorganic pigments that can be used in embodiments of the invention, of titanium, zirconium or cerium oxides, zinc, iron or chromium oxides, ferric blue, manganese violet, ultramarine blue and chromium hydrate. Mention may be made, among the organic pigments that can be used in embodiments, of carbon black, pigments of D & C type, lakes based on cochineal carmine, barium, strontium, calcium or aluminum or diketopyrrolopyrroles (DPP), disclosed in EP-A-542 669, EP-A-787 730, EP-A-787 731 and WO-A-96/08537.

The pearlescent pigments that may be used in embodiments can be chosen from white pearlescent pigments, such as mica covered with titanium oxide or with bismuth oxychloride; colored pearlescent pigments, such as titanium oxide-coated mica with iron oxides, titanium oxide-coated mica with in particular ferric blue or chromium oxide, or titanium oxide-coated mica with an organic pigment of the abovementioned type; and pearlescent pigments based on bismuth oxychloride.

The additional fillers can be present in embodiments in a proportion of 0.01 to 40% by weight, in particular of 0.01 to 30% by weight and especially of 0.02 to 20% by weight, with respect to the total weight of the composition.

In embodiments, the additional fillers may be spherical fillers, such, as for example, talc, zinc stearate, mica, kaolin, polyamide (NYLON®) powders (ORGASOL® from Atochem), polyethylene powders, tetrafluoroethylene polymer (TEFLON®) powders, starch, boron nitride, polymeric microspheres, such as those formed of poly(vinylidene chloride)/acrylonitrile, for example EXPANCEL® (Nobel Industries), or formed of acrylic acid copolymers (POLYTRAP® from Dow Corning), silicone resin microbeads (TOSPEARLS® from Toshiba, for example), and organopolysiloxane elastomers.

The cosmetic composition of embodiments can also comprise water-soluble or fat-soluble dyes in a content ranging from 0.01 to 6% by weight, with respect to the total weight of the composition, in particular ranging from 0.01 to 3% by weight. The fat-soluble dyes are, for example, Sudan red, DC Red 17, DC Green 6, β-carotene, soybean oil, Sudan brown, DC Yellow 11, DC Violet 2, DC Orange 5 and quinoline yellow. The water-soluble dyes are, for example, beetroot juice and methylene blue.

The composition according to embodiments can additionally comprise any ingredient conventionally used in the fields concerned and more especially in the makeup and care field. These ingredients may be chosen, in particular embodiments, from vitamins, antioxidants, thickening agents, trace elements, softening agents, sequestering agents, fragrances, basifying or acidifying agents, preservatives, UV screening agents, hydrophilic or lipophilic active principles, and their mixtures. The amounts of these various ingredients are those conventionally used in the fields concerned and are, for example, from 0.01 to 20% of the total weight of the composition.

Of course, a person skilled in the art will take care to choose this or these optional additional compounds and/or their amounts so that the advantageous properties of the composition according to embodiments are not, or not substantially, detrimentally affected by the addition considered.

The cosmetic composition of embodiments can be obtained according to preparation processes conventionally used in cosmetics.

Cosmetic compositions according to embodiments can in particular be provided in the form of a solid product, such as in the form of a product cast as a stick or as a dish, such as lipsticks or lip balms, cast foundations, concealers, complexion "correctors" and/or "embellishers," eye shadows or blushers.

Cosmetic compositions according to embodiments can be provided in the form of a product for caring for and/or making up the nails, skin and/or lips.

Cosmetic compositions according to embodiments can also be provided in the form of a product for making up the eyelashes. The mascaras thus obtained can be provided in particular in the form of a cake.

Embodiments also relate to processes for the cosmetic treatment of at least one keratinous substance, in particular the skin, hair and/or nails, comprising the application to said substance of a cosmetic composition according to embodiments.

The composition examples below are given by way of illustration, and are not intended to be limiting in nature.

EXAMPLES

Example 1

The following lipstick composition was prepared as follows (percentages by weight):

|  | Percent by weight |
|---|---|
| Polyethylene wax (MW = 500) ("PERFORMALEN 500 ®" from New Phase Technologies) | 10 |
| Microcrystalline wax ("MICROWAX HW ®" from Paramelt) | 2.9 |
| Jojoba butter ("ISO-JOJOBA 50 ®" from Desert Whale Jojoba Company) | 2.5 |
| Dimethicone-coated silica ("SA-SB-300 ®" from Miyoshi) | 4 |
| Pigments | 8.66 |
| Polybutene ("INDOPOL H-100 ®" from Amoco) | 5 |
| Tridecyl trimellitate | 9 |
| Diisostearyl malate | 10 |
| Hydrogenated polyisobutene (965 g/mol) | 24.54 |
| Phenyl trimethicone ("DC 556 ®" from Dow Corning) | 10 |
| Poly(vinyl laurate) | 13.4 |

The lipstick composition of Example 1 shows good application properties of melting, of slip and of softness, and excellent stability over time. It withstands flattening on the back of the hand after storing for 24 hours in an oven controlled at 34, 36 or even 38° C.

Example 2

The following lipstick was prepared as follows (percentage by weight):

|  | Percent by weight |
|---|---|
| 2-Octyldodecanol | 20 |
| Microcrystalline wax ("MICROWAX HW ®" from Paramelt) | 3 |
| Triglycerides of lauric/palmitic/cetylic/stearic acids (50/20/10/10) ("SOFTISAN 100 ®" from Sasol) | 5 |
| Phenyltrimethylsiloxytrisiloxane ("DC 556 ®" from Dow Corning) | 6 |
| Lauryl methacrylate/ethylene glycol dimethacrylate copolymer ("POLYTRAP 6603 ®" from RP Scherer) | 0.5 |
| Polyethylene wax ("PERFORMALEN 500 ®" from New Phase Technologies) | 8 |
| Mixture of glycerides of vegetable fatty acids/isostearic acid/adipic acid ("SOFTISAN 649 ®" from Sasol) | 13 |
| Diisostearyl malate | 18 |
| Pentaerythrityl tetraisostearate | 14 |
| Jojoba butter ("ISO-JOJOBA 50 ®" from Desert Whale Jojoba Company) | 2.55 |
| Pigments | q.s. for 100 |

This composition has good application properties. It confers gloss at a satisfactory level, both immediately after application thereof and after one hour. It is comfortable over time and does not have a sticky effect. It has good stability over time and it is not subject to problems of crystallization or of exudation. It also exhibits good resistance to flattening at 38° C.

What is claimed is:

1. A cosmetic composition, for caring for and/or making up the skin, lips and/or keratinous substances, comprising at least one ester and at least one hydrocarbon wax, said hydrocarbon wax consisting of a mixture selected from the group consisting of at least one hydrocarbon polyethylene wax and at least one microcrystalline wax, wherein the ester is at least one member chosen from the group consisting of esters of a $C_{16}$ to $C_{24}$ ethylenic acid and a $C_{16}$ to $C_{24}$ ethylenic alcohol, said acid and/or said alcohol being of trans configuration, the at least one hydrocarbon wax has a melting point of greater than 70° C., and the ester of at least one member chosen from the group consisting of esters of a $C_{16}$ to $C_{24}$ ethylenic acid and a $C_{16}$ to $C_{24}$ ethylenic alcohol and the hydrocarbon wax consisting of a mixture selected from the group consisting of at least one hydrocarbon polyethylene wax and at least one microcrystalline wax are combined in an ester/wax ratio by weight of from 0.15 to 0.75.

2. The composition as claimed in claim 1, wherein the composition is solid.

3. The composition as claimed in claim 1, wherein said acid does not comprise any hydroxyl groups.

4. The composition as claimed in claim 1, wherein said acid is chosen from $C_{20}$ and $C_{22}$ acids.

5. The composition as claimed in claim 1, wherein said acid is linear.

6. The composition as claimed in claim 1, wherein said acid comprises a single ethylenic unsaturation.

7. The composition as claimed in claim 1, wherein said acid is chosen from the group consisting of octadec-9-enoic acid, oleic acid ($C_{18}$), eicos-11-enoic acid ($C_{20}$), docos-13-enoic acid, erucic acid ($C_{22}$), tetracos-15-enoic acid ($C_{24}$) and their mixtures.

8. The composition as claimed in claim 1, wherein said alcohol is chosen from $C_{20}$ and $C_{22}$ alcohols.

9. The composition as claimed in claim 1, wherein said alcohol is linear.

10. The composition as claimed in claim 1, wherein said alcohol comprises a single ethylenic unsaturation.

11. The composition as claimed in claim 1, wherein said alcohol is chosen from the group consisting of octadec-9-enol ($C_{18}$), eicos-11-enol ($C_{20}$), docos-13-enol ($C_{22}$), tetracos-15-enol ($C_{24}$) and their mixtures.

12. The composition as claimed in claim 1, wherein said ester is chosen from the group consisting of eicos-11-enyl oleate, eicos-11-enyl eicos-11-enoate, docos-13-enyl eicos-11-enoate, tetracos-15-enyl eicos-11-enoate, eicos-11-enyl docos-13-enoate and their mixtures.

13. The composition as claimed in claim 1, said ester being introduced into the composition in the form of jojoba butter.

14. The composition as claimed in claim 13, the jojoba butter being present in the composition in a range of from 0.1 to 40% by weight, with respect to the total weight of the composition.

15. The composition as claimed in claim 1, wherein the hydrocarbon wax with a melting point of greater than 70° C. has a melting point of less than or equal to 105° C.

16. The composition as claimed in claim 1, wherein said hydrocarbon wax with a melting point of greater than 70° C. comprises a mixture of at least one hydrocarbon wax having a melting point of greater than 70° C. and of less than or equal to 80° C. and of at least one wax having a melting point of greater than 80° C. and less than or equal to 105° C.

17. The composition as claimed in claim 16, wherein the ratio by weight of the hydrocarbon wax having a melting point of greater than 70° C. and of less than or equal to 80° C. to the at least one wax having a melting point of greater than 80° C. is from 1/1 to 3/1.

18. The composition as claimed in claim 1, wherein said hydrocarbon polyethylene wax has a molecular weight ranging from 300 to 700.

19. The composition as claimed in claim 1, comprising a mixture of at least one polyethylene wax having a melting point of greater than 70° C. and of less than or equal to 80° C. and of at least one polyethylene wax having a melting point of greater than 80° C. and of less than or equal to 105° C., said waxes being present in a ratio by weight ranging from 1/1 to 3/1.

20. The composition as claimed in claim 19, wherein said ratio is 2/1.

21. The composition as claimed in claim 19, comprising a mixture of at least one polyethylene wax having a melting point of greater than 70° C. and less than or equal to 75° C. and of at least one polyethylene wax having a melting point of greater than 80° C. and of less than or equal to 90° C.

22. The composition as claimed in claim 1, wherein said hydrocarbon wax having a melting point of greater than 70° C. is present in an amount in a range from 0.1 to 25% by weight, with respect to the total weight of the composition.

23. The composition as claimed in claim 1, wherein the composition further comprises at least one silicone oil and/or one nonpolar hydrocarbon oil.

24. The composition as claimed in claim 1, wherein the composition is anhydrous.

25. The composition as claimed in claim 1, wherein the composition further comprises at least one dye and/or at least one pigment and/or at least one additional filler.

26. A method for improving comfort, slip on application and unctuousness of a cosmetic composition while retaining mechanical properties of the cosmetic composition, comprising:
providing at least one ester of a $C_{16}$ to $C_{24}$ ethylenic acid and of a $C_{16}$ to $C_{24}$ ethylenic alcohol, said acid and/or said alcohol being of trans configuration, and at least one hydrocarbon wax with a melting point of greater than 70° C., said hydrocarbon wax being a mixture of at least one hydrocarbon polyethylene wax and at least one microcrystalline wax in a cosmetic composition, wherein the ester and wax are combined in an ester/wax ratio by weight of from 0.15 to 0.75.

* * * * *